United States Patent [19]

Mehta et al.

[11] 4,105,694

[45] Aug. 8, 1978

[54] PROCESS FOR MAKING TRIMETHYLAMINE ACRYLIMIDE

[75] Inventors: Avinash C. Mehta, Belmont; Donald O. Rickter, Arlington; Lloyd D. Taylor, Lexington, all of Mass.

[73] Assignee: Polaroid Corporation, Cambridge, Mass.

[21] Appl. No.: 753,521

[22] Filed: Dec. 22, 1976

[51] Int. Cl.$^2$ .................. C07B 29/00; C07B 102/04
[52] U.S. Cl. ............................................. 260/561 H
[58] Field of Search ................................... 260/561 H

[56] References Cited

U.S. PATENT DOCUMENTS

| | | | |
|---|---|---|---|
| 3,527,802 | 9/1970 | Slagel | 260/561 H |
| 3,664,990 | 5/1972 | Slagel | 260/561 H |
| 3,706,800 | 12/1972 | Hartlagg et al. | 26/561 H |

OTHER PUBLICATIONS

Wagner et al., Synthetic Organic Chemistry, John Wiley & Sons, N.Y., N.Y., 1955, pp. 35–39, 565.

*Primary Examiner*—Allen B. Curtis
*Attorney, Agent, or Firm*—Philip G. Kiely

[57] ABSTRACT

Trimethylamine acrylimide is prepared by condensing a mixture of 3-chloropropionyl chloride, 3-chloropropionic acid and trimethylhydrazinium p-toluenesulfonate; and then converting the thus-formed intermediate to the trimethylamine acrylimide, including the step of deprotonating with base.

2 Claims, No Drawings

PROCESS FOR MAKING TRIMETHYLAMINE ACRYLIMIDE

BACKGROUND OF THE INVENTION

Syntheses of trimethylamine acrylimide are known to the art. For example, in Can. J. Chem., 45, 2625 (1967), the reaction of acrylyl chloride and N,N-dimethylhydrazine is reported.

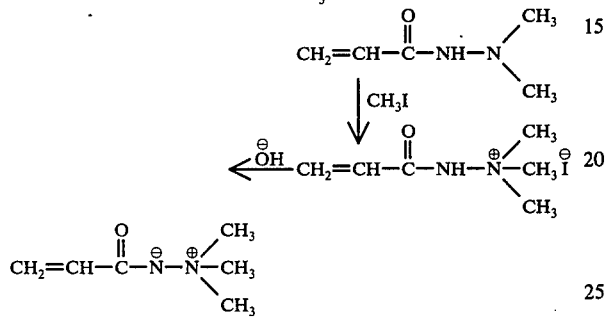

However, yields from this reaction are generally reported as about 11% of trimethylamine acrylimide.

Similarly, U.S. Pat. No. 3,706,800, issued Dec. 19, 1972, discloses the reaction of methyl acrylate and 1,1,1-trimethylhydrazinium chloride.

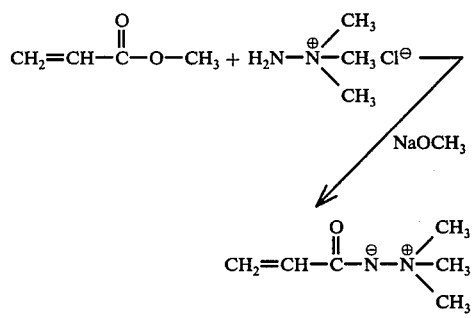

The process disclosed in Example XIV of the above-indicated patent is both impractical and uneconomical for large scale preparation on account of low yields (about 35.1%), long reaction time (7 hours), and the costly and tedious step of vacuum sublimation for isolation of the pure product.

A novel and simple process has now been found for the preparation of trimethylamine acrylimide.

SUMMARY OF THE INVENTION

The present invention essentially involves condensation between a mixture of 3-chloropropionyl chloride, 3-chloropropionic acid and trimethylhydrazinium p-toluenesulfonate. The resulting intermediate is easily converted to the aminimide either by a base catalyzed dehydrochlorination or by first rearranging the intermediate thermally to an acrylylhydrazinium chloride, which is then easily deprotonated with a mild base.

DETAILED DESCRIPTION OF THE INVENTION

As stated above, the present invention involves condensation between a mixture of 3-chloropropionyl chloride, 3-chloropropionic acid and trimethylhydrazinium p-toluenesulfonate and converting the thus-formed intermediate to the trimethylamine acrylimide. The reaction may be represented as follows:

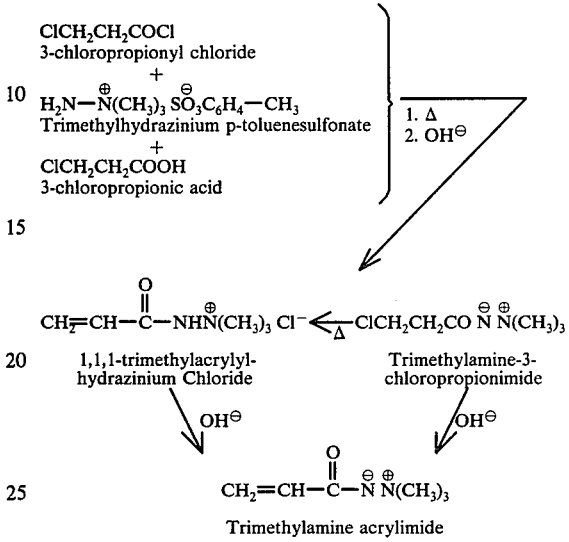

The process of the present invention comprises the step of condensing a mixture of 3-chloropropionyl chloride, 3-chloropropionic acid and trimethylhydrazinium p-toluenesulfonate at a temperature above 80° C, adjusting the pH of the solution to about 8, heating the thus-formed trimethylamine-3-chloropropionimide under anhydrous conditions to provide thermal rearrangement to 1,1,1-trimethyl acrylylhydrazinium chloride and then deprotonating with base to provide trimethylamine acrylimide.

The 3-chloropropionyl chloride and 3-chloropropionic acid are articles of commerce and readily available. The trimethylhydrazinium p-toluenesulfonate is prepared according to the procedure set forth in J. Org. Chem., 36(8), 1155 (1971).

The following non-limiting example illustrates the novel method of the present invention.

EXAMPLE 1

A mixture of 369g (1.50 moles) of 1,1,1-trimethylhydrazinium tosylate, 150g (1.38 moles) of 3-chloropropionic acid, and 165ml (about 220g; 1.73 moles) of 3-chloropropionyl chloride was heated in a 2-liter flask that had been flushed with dry nitrogen. The reaction mixture became a clear, amber solution at 88° C. The solution was stirred and heated at 100°–110° C for one hour. The reaction mixture was cooled to room temperature and then extracted with four 500ml portions of ethyl ether, stirring vigorously for 15 minutes each time, to remove chloropropionic acid. The residual solid was dissolved in about 375ml of methanol and titrated to pH 8 by addition of 10% (weight/volume) potassium hydroxide in methanol. The precipitated salts were filtered and the filtrate evaporated to dryness on a rotary evaporator at 25° to 40° C. The residue was extracted with benzene and the extract filtered. Stripping the solvent left white crystalline trimethylamine 3-chloropropionimide (197g; 79.77% yield) m.p. 99°–105°. Infrared spectrum (KBr) showed absorption characteristic of the structure at 1590 cm$^{-1}$. NMR was consistent with the structure.

It should be noted that the removal of chloropropionic acid by ether extraction provides for the recovery and recycling of substantially all of the chloropropionic acid, as well as the ether, since the chloropropionic acid does not enter into the reaction.

The intermediate trimethylamine-3-chloropropionimide can be converted to the corresponding aminimide in one of two ways.

EXAMPLE 1A

Single-Step Process

Trimethylamine-3-chloropropionimide (13g; 0.078 mole) was stirred with 100ml of 10% (weight/volume) potassium hydroxide in methanol for 4 hours. The precipitated salts were filtered and washed twice with 25ml of cold methanol. The filtrate was stripped on a rotary evaporator to a viscous mixture which was azeotroped twice with 50ml portions of benzene. The residue was stirred with 100ml of benzene and the solution filtered. Concentration of the filtrate on the rotary evaporator gave 7.3g (71.9% yield) of trimethylamine acrylimide, m.p. 85°–95°. It gave a negative Beilstein test for halogen and in the infrared spectrum (KBr) showed absorption characteristic of the structure at 1570 cm$^{-1}$. NMR was consistent with the structure.

EXAMPLE 1B

Two-Step Process

1. Thermal Rearrangement of Trimethylamine-3-chloropropionimide to 1,1,1-Trimethyl acrylyl-hydrazinium chloride.

Trimethylamine-3-chloropropionimide (48.2g; 0.293 mole) was heated under anhydrous conditions at 119° (oil bath temperature) for 10 min. The solid mass was allowed to cool and then scraped from the flask. A quantitative yield of 1,1,1-trimethyl acrylylydrazinium chloride, m.p. 181°–82° (dec), was obtained. Infrared spectrum (KBr) showed absorption at 3420, 3120, 3010, 1685, 1620cm$^{-1}$. NMR was consistent with the structure.

An analytically pure sample, m.p. 181° (dec), was obtained through recrystallization from nitromethane.

Anal. Calcd. for C$_6$H$_{13}$N$_2$O Cl: C, 43.77; H, 7.95; N, 17.02; Cl, 21.53. Found: C, 43.62; H, 7.89; N, 17.03; Cl, 21.46

2. Deprotonation of 1,1,1-Trimethyl acrylylhydrazinium chloride to Trimethylamine acrylimide.

A solution of 6.3g (0.038 mole) of 1,1,1-trimethyl acrylylhydrazinium chloride in 50ml of dry methanol was titrated to a phenolphthalein end point using 10% (weight/volume) potassium hydroxide in methanol. The reaction mixture was stripped of the solvent on the rotary evaporator at about 35°. The residual hygroscopic solid was extracted with 50ml of benzene and the benzene extract filtered. Removal of solvent from the colorless filtrate on the rotary evaporator gave 4.70g (96% yield) of white crystals, m.p. 85°–95°. This material was identical in all respects (physical and spectral properties with the material obtained by the single-step process, Example 1A, described above.

The novel method of the present invention is rapid, economical and provides yields of the purified final product of about 76–77%.

Trimethylamine acrylimide prepared by the novel process of the present invention is known to the art and is useful in its ability to be rearranged to the corresponding isocyanate. Likewise, the homo- and co-polymers obtained from trimethylamine acrylimide can be rearranged to the corresponding polyisocyanates which are well known cross-linking agents useful in the formation of polyurethanes. More details on the utility of acrylimides will be found in above-identified U.S. Pat. No. 3,706,800.

What is claimed is:

1. The process which comprises the steps of condensing a mixture of 3-chloropropionyl chloride, 3-chloropropionic acid and trimethylhydrazinium p-toluenesulfonate, adjusting the pH to about 8 and converting the thus formed intermediate to trimethylamine acrylimide by thermal rearrangement and then a deprotonation step.

2. The process which comprises the step of condensing a mixture of 3-chloropropionyl chloride, 3-chloropropionic acid and trimethylhydrazinium p-toluenesulfonate at a temperature above 80° C, adjusting the pH of the solution to about 8, heating the thus-formed trimethylamine-3-chloropropionimide under anhydrous conditions to provide thermal rearrangement to 1,1,1-trimethyl acrylylhydrazinium chloride and then deprotonating with base to provide trimethylamine acrylimide.

* * * * *